(12) United States Patent
Yu et al.

(10) Patent No.: US 11,337,668 B2
(45) Date of Patent: May 24, 2022

(54) COMPUTED TOMOGRAPHY SYSTEM AND METHOD FOR IMAGE IMPROVEMENT USING PRIOR IMAGE

(71) Applicant: Accuray, Inc., Sunnyvale, CA (US)

(72) Inventors: Zhicong Yu, Highland Hts., OH (US); Daniel Gagnon, Twinsburg, OH (US)

(73) Assignee: Accuray, Inc., Sunnyvale, CA (US)

( * ) Notice: Subject to any disclaimer, the term of this patent is extended or adjusted under 35 U.S.C. 154(b) by 174 days.

(21) Appl. No.: 16/694,166

(22) Filed: Nov. 25, 2019

(65) Prior Publication Data

US 2020/0175733 A1 Jun. 4, 2020

Related U.S. Application Data

(60) Provisional application No. 62/878,364, filed on Jul. 25, 2019, provisional application No. 62/843,796, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01); *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01);
(Continued)

(58) Field of Classification Search
CPC . G06T 11/005; G06T 11/008; G06T 2211/432
See application file for complete search history.

(56) References Cited

U.S. PATENT DOCUMENTS

| 4,190,773 | A | 2/1980 | Braden |
| 5,615,279 | A | 3/1997 | Yoshioka et al. |

(Continued)

FOREIGN PATENT DOCUMENTS

| DE | 10 2006 007058 A1 | 7/2007 |
| EP | 1062914 A1 | 12/2000 |

(Continued)

OTHER PUBLICATIONS

International Search Report and Written Opinion from PCT/US2019/063080 dated Mar. 16, 2020.
(Continued)

*Primary Examiner* — Dani Fox
(74) *Attorney, Agent, or Firm* — Calfee, Halter & Griswold, LLP

(57) ABSTRACT

A computed tomography (CT) system and method is provided. The CT system is used to carry out an image improvement method in which a prior or previously-acquired patient image can be used to supplement or otherwise improve an acquired CT image, wherein the acquired projection data representative of the acquired CT image might be truncated or otherwise incomplete/insufficient to accurately and stably recover the scanned object/patient.

20 Claims, 11 Drawing Sheets

Related U.S. Application Data filed on May 6, 2019, provisional application No. 62/836,352, filed on Apr. 19, 2019, provisional application No. 62/836,357, filed on Apr. 19, 2019, provisional application No. 62/821,116, filed on Mar. 20, 2019, provisional application No. 62/813,335, filed on Mar. 4, 2019, provisional application No. 62/801,260, filed on Feb. 5, 2019, provisional application No. 62/800,287, filed on Feb. 1, 2019, provisional application No. 62/796,831, filed on Jan. 25, 2019, provisional application No. 62/773,700, filed on Nov. 30, 2018, provisional application No. 62/773,712, filed on Nov. 30, 2018.

(51) Int. Cl.
| | |
|---|---|
| *A61B 6/03* | (2006.01) |
| *A61B 6/06* | (2006.01) |
| *A61B 6/02* | (2006.01) |
| *A61N 5/10* | (2006.01) |
| *A61B 6/08* | (2006.01) |
| *G06T 7/30* | (2017.01) |
| *A61B 5/055* | (2006.01) |
| *A61B 6/04* | (2006.01) |

(52) U.S. Cl.
CPC .............. *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(56) References Cited

U.S. PATENT DOCUMENTS

| | | | |
|---|---|---|---|
| 6,233,478 | B1 | 5/2001 | Liu |
| 6,307,909 | B1 | 10/2001 | Flohr et al. |
| 7,050,528 | B2 | 5/2006 | Chen |
| 7,336,759 | B2 | 2/2008 | Nukui |
| 7,660,380 | B2 | 2/2010 | Boese et al. |
| 8,116,430 | B1 | 2/2012 | Sharpio et al. |
| 8,467,497 | B2 | 6/2013 | Lu et al. |
| 8,588,363 | B2 | 11/2013 | Flohr |
| 9,400,332 | B2 | 7/2016 | Star-Lack et al. |
| 2003/0007601 | A1 | 1/2003 | Jaffray et al. |
| 2003/0076927 | A1 | 4/2003 | Shigeyuki et al. |
| 2004/0091079 | A1 | 5/2004 | Zapalac |
| 2004/0202360 | A1 | 10/2004 | Besson |
| 2005/0053188 | A1 | 3/2005 | Gohno |
| 2005/0251029 | A1 | 11/2005 | Khamene et al. |
| 2006/0109954 | A1 | 5/2006 | Gohno |
| 2006/0262894 | A1 | 11/2006 | Bernhadt et al. |
| 2007/0127621 | A1 | 6/2007 | Grass et al. |
| 2007/0189444 | A1 | 8/2007 | Van Steven-Daal et al. |
| 2008/0103834 | A1 | 5/2008 | Reiner |
| 2008/0112532 | A1 | 5/2008 | Schlomka et al. |
| 2009/0080603 | A1 | 3/2009 | Shukla et al. |
| 2009/0135994 | A1 | 5/2009 | Yu et al. |
| 2009/0161826 | A1 | 6/2009 | Gertner et al. |
| 2009/0225932 | A1 | 9/2009 | Zhu et al. |
| 2009/0283682 | A1 | 11/2009 | Star-Lack et al. |
| 2009/0304142 | A1 | 12/2009 | Ruimi et al. |
| 2010/0046819 | A1 | 2/2010 | Noo |
| 2010/0142791 | A1 | 6/2010 | Tsuji |
| 2010/0208964 | A1* | 8/2010 | Wiegert .............. G01T 1/1648 382/131 |
| 2011/0142312 | A1 | 6/2011 | Toth |
| 2011/0255656 | A1 | 10/2011 | Star-Lack et al. |
| 2012/0014582 | A1 | 1/2012 | Schaefer et al. |
| 2012/0207370 | A1 | 8/2012 | Fahimian et al. |
| 2012/0263360 | A1 | 10/2012 | Zhu et al. |
| 2012/0294504 | A1 | 11/2012 | Kyriakou |
| 2013/0101082 | A1 | 4/2013 | Jordan et al. |
| 2013/0294570 | A1 | 11/2013 | Hansis |
| 2014/0018671 | A1 | 1/2014 | Li et al. |
| 2014/0086383 | A1 | 3/2014 | Huwer et al. |
| 2014/0169652 | A1 | 6/2014 | Vic et al. |
| 2015/0297165 | A1 | 10/2015 | Tanaka et al. |
| 2015/0305696 | A1 | 10/2015 | Yamakawa et al. |
| 2016/0016009 | A1 | 1/2016 | Manzke et al. |
| 2016/0120486 | A1 | 5/2016 | Goto et al. |
| 2016/0220844 | A1 | 8/2016 | Paysan et al. |
| 2016/0262709 | A1 | 9/2016 | Siewerdsen et al. |
| 2017/0000428 | A1 | 1/2017 | Goto |
| 2017/0197098 | A1 | 7/2017 | Hirasawa et al. |
| 2017/0205360 | A1 | 7/2017 | Cinquin et al. |
| 2017/0278277 | A1 | 9/2017 | Morf et al. |
| 2017/0332982 | A1 | 11/2017 | Koehler |
| 2018/0028143 | A1 | 2/2018 | Wiggers et al. |
| 2018/0070894 | A1 | 3/2018 | Osaki et al. |
| 2018/0192978 | A1 | 7/2018 | Naylor |
| 2018/0345042 | A1* | 12/2018 | Voronenko .......... A61N 5/1065 |
| 2019/0099149 | A1 | 4/2019 | Li |
| 2020/0016432 | A1 | 1/2020 | Maolinbay |
| 2020/0121267 | A1 | 4/2020 | Deutschmann |
| 2020/0402644 | A1 | 12/2020 | Zhou et al. |
| 2021/0165122 | A1 | 6/2021 | Morton |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005/112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015/103184 A1 | 7/2015 |
| WO | 2018/156968 A1 | 8/2018 |
| WO | 2018/183748 A1 | 10/2018 |

OTHER PUBLICATIONS

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.

(56) References Cited

OTHER PUBLICATIONS

International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11 , Radiology, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Notice of Allowance from U.S. Appl. No. 16/694,190 dated Jun. 23, 2021, 8 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Office Action from U.S. Appl. No. 16/694,145 dated Mar. 17, 2021.
Office Action from U.S. Appl. No. 16/694,190 dated Mar. 26, 2021.
Office Action from U.S. Appl. No. 16/694,230 dated Apr. 1, 2021.
Clackdoyle, R. and Desbat, L., 2015. Data consistency conditions for truncated fanbeam and parallel projections. Medical physics, 42(2), pp. 831-845.
Defrise, M., Noo, F. and Kudo, H., 2000. A solution to the long-object problem in helical cone-beam tomography. Physics in Medicine & Biology, 45(3), p. 623.
Hsieh, J., Chao, E., Thibault, J., Grekowicz, B., Horst, A., McOlash, S. and Myers, T.J., 2004. A novel reconstruction algorithm to extend the CT scan field-of-view. Medical physics, 31(9), pp. 2385-2391.
Katsevich, A., 2004. An improved exact filtered backprojection algorithm for spiral computed tomography. Advances in Applied Mathematics, 32(4), pp. 681-697.
Li H, Mohan R, and Zhu XR, Scatter kernel estimation with an edge-spread function method for cone-beam computed tomography imaging, Phys. Med. Biol. 51 (2008) 4567-4586.
Maslowski, A., Wang, A., Sun, M., Wareing, T., Davis, I. and Star-Lack, J., 2018. Acuros CTS: A fast, linear Boltzmann transport equation solver for computed tomography scatter—Part I: Core algorithms and validation. Medical physics.
Ning, R., Tang, X. and Conover, D., 2004. X-ray scatter correction algorithm for cone beam CT imaging. Medical physics, 3 I (5), pp. 1195-1202.
Siewerdsen, J.H., Daly, M.J., Bakhtiar, B., Moseley, D.J., Richard, S., Keller, H. and Jaffray, D.A., 2006. A simple, direct method for x-ray scatter estimation and correction in digital radiography and cone-beam CT. Medical Physics, 33(1), pp. 187-197.
Sun, M. and Star-Lack, J.M., 2010. Improved scatter correction using adaptive scatter kernel superposition. Physics in Medicine & Biology, 55(22), p. 6695-6720.
Tang, Q., Matsuura, M. and Yu, Z., 2018, Salt Lake City, UT. A sinogram extrapolation method for CT field of view extension. Proceedings of the Fifth CT Meeting, pp. 206-209.
Office Action from U.S. Appl. No. 16/694,202 dated Apr. 9, 2021.
Lifeng Yu, et al., Radiation dose reduction in computed tomography: techniques and future perspective. Imaging Med. Oct. 2009; 1 (1 ), pp. 65-84.
Zbijewski, W. et al. Efficient Monte Carlo based scatter artifact reduction in cone-beam micro-CT. IEEE transactions on medical imaging, 25(7), pp. 817-827.
Zhu, L., Bennett, N.R. and Fahrig, R., 2006. Scatter correction method for X-ray CT using primary modulation: Theory and preliminary results. IEEE transactions on medical imaging, 25(12), pp. 1573-1587.
Noo et al., "A new scheme for view-dependent data differentiation in fan-beam and cone-beam computed tomography" Phys. Med. Biol. 52 (2007) pp. 5393-5414.
Kudo et al., Exact and approximate algorithms for helical cone-beam CT, Apr. 27, 2004, pp. 1-26.
Kunze, et al., "Cone beam reconstruction with displaced flat panel detector", 10th International Meeting on Fully Three-Dimensional Image Reconstruction in Radiology and Nuclear Medicine, pp. 138-141.
Schafer, et al., "FBP and BPF reconstruction methods for circular X-ray tomography with off-center detector", Medical Physics, vol. 38, No. 7, Jul. 2011, pp. S85-S94.
Schafer, et al., "Cone-beam filtered back-projection for circular X-ray tomography with off-center detector", 10th International Meeting on Fully Three-Dimensional Image Reconstruction in Radiology and Nuclear Medicine, pp. 86-89.
Zamyatin et al., "Helical cone beam CT with an asymmetrical detector," Med. Phys. 32 (10), Oct. 2005, pp. 3117-3127.
Office Action from U.S. Appl. No. 16/694,161 dated Sep. 13, 2021, 18 pages.
Zhu, et al. Noise suppression in scatter correction for cone-beam CT, American Association of Physicists in Medicine, 2009, pp. 741-752, vol. 36, No. 3.
Anas, et al. High-quality 3D correction of ring and radiant artifacts in flat panel detector-based cone beam vol. CT imaging, Phys. Med. Biol., 2011, pp. 6495-6519, vol. 56.
Bootsma, et al., Spatial frequency spectrum of the x-ray scatter distribution in CBCT projections, Med. Phys., Nov. 2013, pp. 111901-1-111901-15, vol. 40, No. 11.
International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correction methods in cone beam CT. Part 2: Scatter estimation approaches, Med. Phys. Sep. 2011, pp. 5186-5199, vol. 38, No. 9.
Yang, et al., Scattering estimation for cone-Beam CT Using Local Measurement Based on Compressed Sensing, IEEE transactions on Nuclear Science, Mar. 2018, pp. 941-949, vol. 65, No. 3.

* cited by examiner

US 11,337,668 B2

COMPUTED TOMOGRAPHY SYSTEM AND METHOD FOR IMAGE IMPROVEMENT USING PRIOR IMAGE

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019). This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled ";" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019 (entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019 (entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to computed tomography (CT) imaging, and, more particularly, to a CT system and method for image improvement using information from a prior or otherwise previously-acquired image, including as part of image-guided radiation treatment (IGRT).

BACKGROUND

Computed tomography (CT) imaging generally involves exposing a patient or a portion of a patient to a radiation source and positioning a radiation detector to receive x-ray radiation from the radiation source. The radiation source and detector are moved to a variety of positions around the patient, and the received radiation is used to generate an image of the patient. In some instances, it is possible that a patient or some portion of a patient is illuminated insufficiently by the radiation source, giving rise to truncated image data or insufficient projections.

Radiotherapy is one area where CT imaging is being employed with greater frequency. Radiotherapy is often carried out by directing a high-energy beam of x-rays (e.g., at an energy level in the megavoltage range) toward a tumor or other region of interest within a patient. The goal of the treatment is to focus the high-energy x-ray beam on the region of interest, while minimizing the exposure of surrounding tissue. So-called image-guided radiation treatment (IGRT) can make use of CT imaging to collect images of a patient for use in image-based pre-delivery steps, which can include treatment planning. CT Image acquisition can also be used to confirm that therapeutic radiation beams are correctly directed to and treating the region of interest.

BRIEF SUMMARY

In one embodiment, a method for improving scan image quality using prior image data includes receiving image data corresponding to a prior image of a patient, obtaining projection image data of the patient, wherein the obtained projection image data is truncated, reconstructing a patient image based on the obtained projection image data of the patient, registering the prior image with the reconstructed patient image, generating virtual projection data based on the registered prior image, and reconstructing a supplemented projection image data set to create an improved patient image, wherein the supplemented projection image data set comprises the obtained projection image data and the virtual projection data.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

Figure 1:
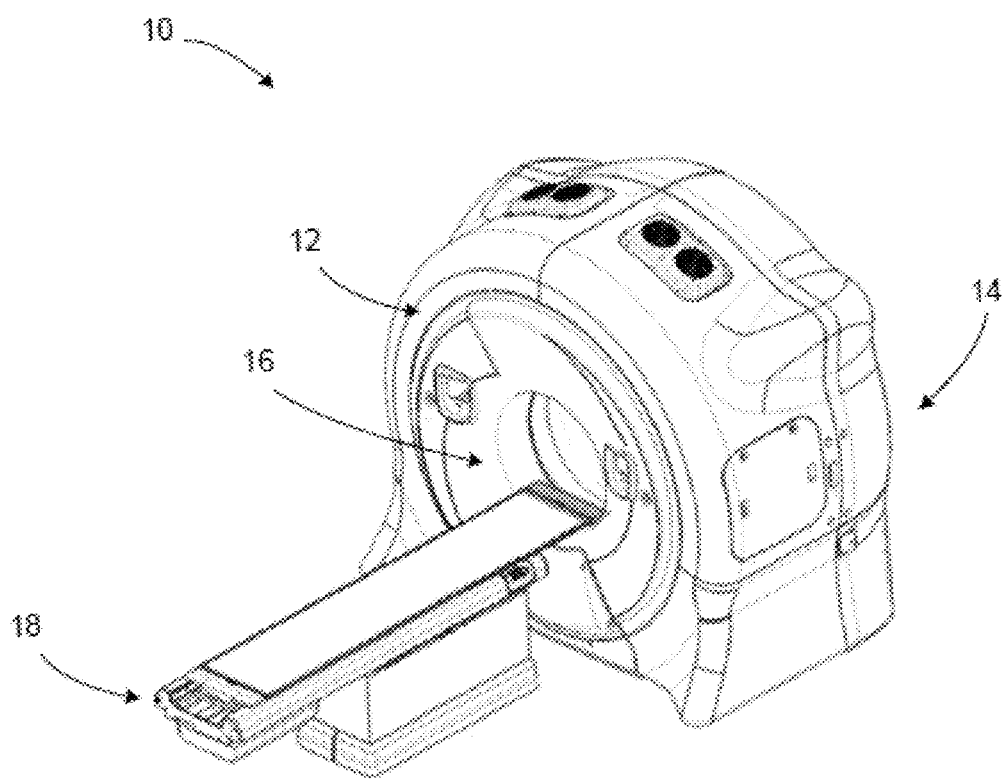
FIG. 1 is a perspective view of an exemplary radiotherapy delivery device in accordance with one aspect of the disclosed technology.

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

As is discussed in more detail below, aspects of the disclosed technology relate to CT imaging systems and methods, where a prior or otherwise previously-acquired patient image (e.g., a planning image) can be used to supplement or otherwise improve an acquired CT image, including when the acquired projection data representative of the acquired CT image might be truncated or otherwise incomplete/insufficient to accurately represent the scanned object/patient. In some embodiments, certain attributes and/or information associated with the prior image are used to supplement an acquired image, not the prior image itself.

The present disclosure recognizes that acquired data in a CT imaging procedure (e.g., in a fan beam or a cone-beam CT (CBCT) imaging procedure) might not be sufficient to reconstruct images of sufficient quality (e.g., for analytical reconstruction method), which could ultimately result in image artifacts (e.g., cone-beam artifacts). In one example, a typical CBCT source trajectory is circular. However, data acquired from such a trajectory are not sufficient for exact image reconstruction for image pixels located outside the circular plane. This data insufficiency results in cone-beam artifacts, and the artifacts can become worse when the imaging plane moves away from the trajectory plane (or the longitudinal coverage of the detector becomes larger).

Another typical cone-beam data acquisition geometry is helical. For such a trajectory, due to limited projection data, the volume of interest for good image quality is typically shorter than the scan length in the longitudinal or axial direction. At the beginning or the end of the helical trajectory, there might not be enough projection data for good image reconstruction, or the reconstructed images might contain too many artifacts.

In these examples, the above-mentioned image artifacts are usually low frequency in the axial direction. One typical solution might be to acquire more data using an additional trajectory. Taking the circular trajectory as an example, an additional line attached to a circular trajectory would provide additional data for exact image reconstruction in an extended longitudinal volume. However, such additional scanning will require additional time, increase patient dose, and/or potentially complicate the imaging workflow.

The present disclosure recognizes that the above-mentioned missing or insufficient data usually corresponds to low frequency. A good approximation of these additional data could be sufficient, e.g., for image reconstruction. Aspects of the disclosed technology can use a prior or previously-acquired image (e.g., a planning CT image) and a virtual projector applied on this dataset to generate additional data for improved image reconstruction. Such a method is applicable to many source trajectories including, but not limited to, a circular trajectory and a helical trajectory. It will be further discussed that such a method can be combined with one or more iterative image reconstruction techniques.

While aspects of the disclosed technology will be described in connection with the prior or previously-acquired image being a prior planning image (e.g., an image acquired before treatment for the purposes of generating a treatment plan for use in connection with an IGRT procedure), it will be appreciated that aspects of the disclosed technology can be carried out in a general imaging environment (e.g., in a standard computed tomography imaging environment separate from any IGRT application).

For example, in some embodiments, the disclosed technology relates to a CT system separate from a radiotherapy system. In other embodiments, a radiotherapy delivery device and method can make use of an integrated low-energy radiation source for CT for use in conjunction with or as part of IGRT. In particular, for example, the radiotherapy delivery device and method can combine a low-energy radiation source for imaging in a gantry with a high-energy radiation source for therapeutic treatment. In one embodiment, the low-energy radiation source is a kilovolt (kV) radiation source as part of a CT system and the high-energy radiation source for therapeutic treatment is a megavolt (MV) radiation source. Embodiments below mentioning kV radiation sources may also utilize other low-energy radiation sources.

As mentioned above, the image acquisition system need not be associated with an IGRT system with a dedicated kV imaging source. For example, the involved image acquisition system may include a MV x-ray tube and MV x-ray detector, a kV x-ray tube and a kV x-ray detector, or combinations of both. As discussed in more detail below, these imaging sources and detectors may be mounted in various combinations on a CT-like gantry (e.g., with a slip-ring), on a robotic arm, on two robotic arms, and/or on other mounting devices.

In accordance with one embodiment, the method can be carried out on the system shown in FIG. 1 and FIG. 2 and described below. However, it will be appreciated that the imaging method can be carried out on a different computed tomography imaging system (e.g., a MV CT system and/or a kV CT system, where the source and/or the detector are operatively coupled to one or more robotic arms, such as a C-arm system) without departing from the scope of the disclosed technology.

Figure 2:
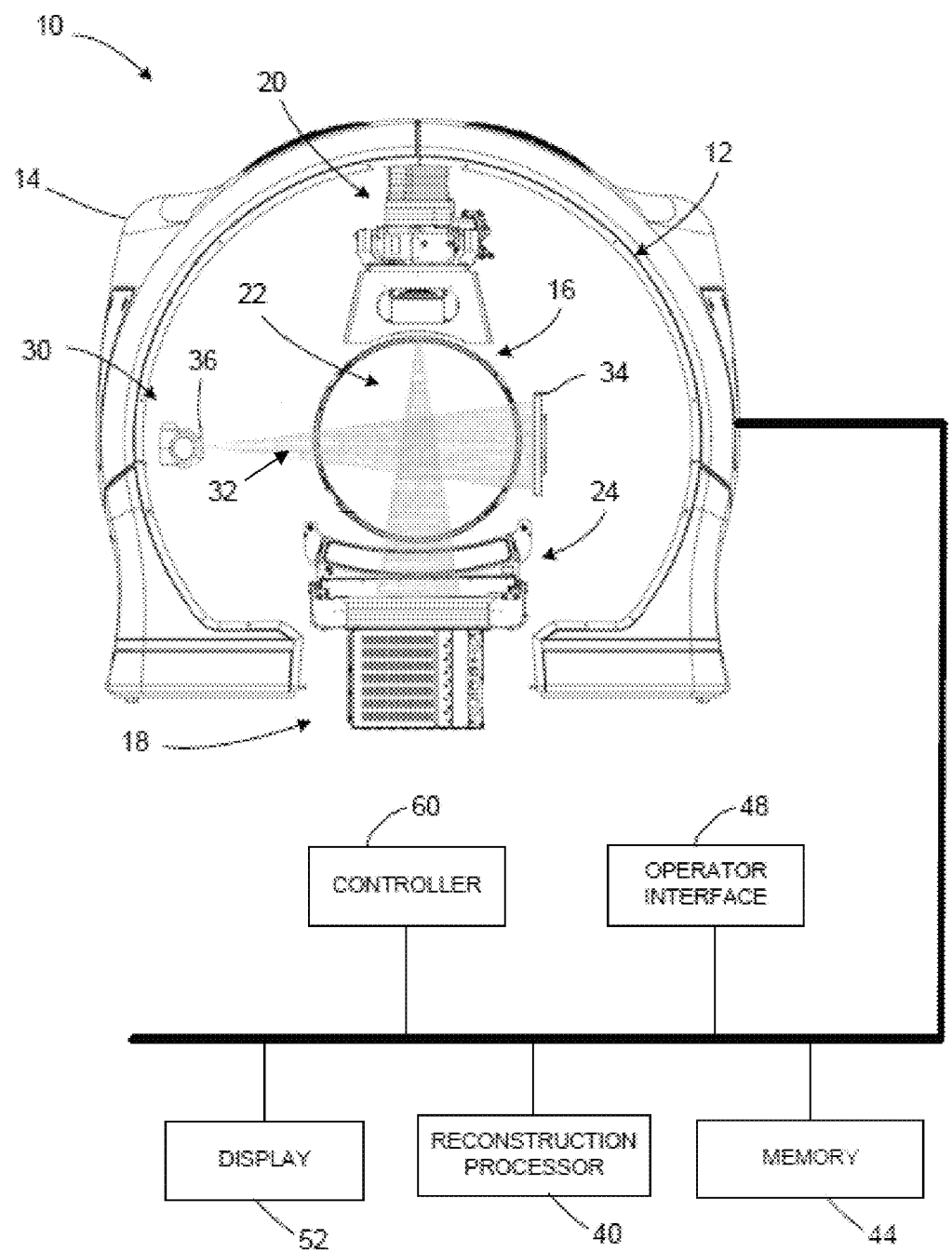
FIG. 2 is a diagrammatic illustration of an exemplary radiotherapy delivery device in accordance with one aspect of the disclosed technology.

With reference to FIG. 1 and FIG. 2, a radiotherapy device 10 is provided. It will be appreciated that the radiotherapy device 10 can be used for a variety of applications, including, but not limited to, image-guided radiation treatment or therapy (IGRT). The radiotherapy device 10 can be used to carry out the imaging methods described more fully below. The radiotherapy device 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 revolutions per minute (rpm) or more (e.g., using fast slip ring rotation, including, e.g., up to 10 rpm, up to 20 rpm, up to 60 rpm, or more rpm). The rotatable gantry 12 defines a gantry bore 16 into and through which a patient can be moved and positioned for imaging and/or treatment. In accordance with one embodiment the rotatable gantry 12 is configured as a slip ring gantry to provide continuous rotation of an imaging radiation source and an associated radiation detector while providing sufficient bandwidth for the imaging data received by the detector. A slip-ring gantry can eliminate gantry rotations in alternating directions in order to wind and unwind cables carrying the power and signals associated with the device. As is discussed more fully below, such a configuration can allow for continuous helical (e.g., fan-beam, cone-beam, etc.) computed tomography, even when integrated into an IGRT system. As mentioned above, a major issue with single rotation CBCT is insufficient sampling on all slices except for the central slice (the one containing the rotation). This can be overcome by helical trajectory cone-beam imaging.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. In some embodiments, the patient support can also be moved in a limited range up and down, left and right once it is in the bore 16 to adjust the patient position for optimal treatment. It will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The device 10 is capable of volume-based and planar-based imaging acquisitions. For example, in various embodiments, the device 10 may be used to acquire volume images and/or planar images and execute the associated processing methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) linear movement, speed, and/or trajectories, etc., and combinations thereof may be used, including in combination with the various embodiments of radiotherapy devices 10 described above.

As shown in FIG. 2, the radiotherapy device 10 includes a first source of radiation 20 coupled to or otherwise supported by the rotatable gantry 12. In accordance with one embodiment, the first source of radiation 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation without departing from the scope of the disclosed technology. In one embodiment, the first source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the first source of radiation 20 has a higher energy level (peak and/or average, etc.) than the second source of radiation 30.

The imaging system, described in detail below, comprises a second source of radiation 30, which may be an independent x-ray imaging source producing relatively low intensity and lower energy imaging radiation. In one embodiment, the second source of radiation 30 is an x-ray source, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments.

It will be further appreciated that the first source of radiation 20 can emit one or more beams of radiation (indicated generally by 22) toward a region-of-interest (ROI) within a patient supported on the patient support 18. The first source of radiation can emit one or more beams of radiation in accordance with a treatment plan. It also will be appreciated that the treatment plan can include detailed parameters regarding source angular position, beam geometry, beam intensity, modulation, exposure, and the like.

In one embodiment, the first source of radiation 20 is a LINAC producing therapeutic radiation (e.g., MV) and the imaging system comprises an independent second source of radiation 30 producing relatively low intensity and lower energy imaging radiation (e.g., kV). In other embodiments, the first source of radiation 20 could be a radioisotope, such as, for example, Co-60, which can generally have energy >1 MeV. The first source of radiation 20 can emit one or more beams of radiation (indicated generally by 22) toward a region-of-interest (ROI) within a patient supported on the patient support 18 in accordance with a treatment plan.

As discussed in detail below, sources of radiation 20, 30 may be used in conjunction with one another to provide higher quality and better utilized images. In other embodiments, at least one additional radiation source can be coupled to the rotatable gantry 12 and operated to acquire projection data at a peak photon energy distinct from the peak photon energies of sources of radiation 20, 30.

Although FIGS. 1 and 2 depict a radiotherapy device 10 with a radiation source 20 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

First detector 24 can be coupled to or otherwise supported by the rotatable gantry 12 and positioned to receive radiation 22 from the first source of radiation 20. The first detector 24 can detect or otherwise measure the amount of radiation not attenuated and therefore infer what was in fact attenuated by the patient or associated patient ROI (by comparison to what was initially generated). The first detector 24 can detect or otherwise collect attenuation data from different angles as the first radiation source 20 rotates around and emits radiation toward the patient. The collected attenuation data can be processed and reconstructed into one or more images of the patient's body.

The imaging system integrated within the radiotherapy device 10 can provide current images that are used to set up (e.g., align and/or register), plan, and/or guide the radiation delivery procedure (treatment). Typical set-up is accomplished by comparing current (in-treatment) images to pre-treatment image information (e.g., prior or otherwise previously-acquired image information). Pre-treatment image information may comprise, for example, CT data, CBCT data, magnetic resonance imaging (MRI) data, positron emission tomography (PET) data or 3D rotational angiography (3DRA) data, and/or any information obtained from these or other imaging modalities. In some embodiments, the imaging system can track in-treatment patient, target, or ROI motion.

Conventional in-treatment images typically comprise CBCT or two-dimensional images (typically x-ray). X-rays can be acquired at one or more different points of view (e.g., stereoscopic x-ray images), which can be compared with two-dimensional digitally reconstructed radiographs (DRRs) derived from the three-dimensional pre-treatment image information. CBCT can directly construct a 3D volumetric image from 2D projections of the target volume. As is known in the art, in one embodiment, CBCT has the ability to form a 3D image volume from a single gantry rotation about the target volume with a more isotropic spatial resolution. In other embodiments, CBCT can utilize helical scan trajectories. However, scatter, incomplete data, and/or artifacts, as mentioned above can be significant problems for CBCT systems, limiting image quality. As can be appreciated, using conventional techniques, these and other conventional radiotherapy in-treatment imaging systems lack the ability to produce high-quality and/or complete images suitable for image-based pre-delivery steps, including real-time treatment planning.

As shown in FIG. 2, the imaging system integrated within the radiotherapy device 10 includes a second source of radiation 30 coupled to or otherwise supported by the rotatable gantry 12. As discussed above, the second source of radiation 30 can be configured as a source of imaging radiation (e.g., kV) for high-quality in-treatment images (indicated generally as 32) having an energy level less than the first source 20 of therapeutic radiation.

A second detector 34 (e.g., two-dimensional flat detector or curved detector) can be coupled to or otherwise supported by the rotatable gantry 12. The second detector 34 is positioned to receive radiation from the second source of radiation 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the second radiation source 30 rotates around and emits radiation toward the patient.

A collimator or beamformer assembly (indicated generally as 36) is positioned relative to the second source of radiation 30 to selectively control and adjust a shape of a radiation beam 32 emitted by the second radiation source 30 to selectively expose a portion or region of the active area of the second radiation detector 34. The collimator 36 can also control how the radiation beam 32 is positioned on the detector 34. In one embodiment, the collimator 36 could have one degree/dimension of motion (e.g., to make a thinner or fatter slit). In another embodiment, the collimator 36 can have two degrees/dimensions of motion (e.g., to make various sized rectangles). In other embodiments, the collimator 36 may be capable of various other dynamically-controlled shapes, including, for example, parallelograms. All of these shapes may be dynamically adjusted during a scan. In some embodiments, blocking portions of the collimator can be rotated and/or translated.

The collimator/beamformer 36 may be configured in a variety of ways that allow it to adjust the shape of the radiation beam 32 emitted by the second source of radiation 30. For example, the collimator 36 can be configured to include a set of jaws or other suitable members that define and selectively adjust the size of an aperture through which the radiation beam from the second source of radiation 30 may pass in a collimated manner. In accordance with one exemplary configuration, the collimator 36 can include an upper jaw and a lower jaw, where the upper and lower jaws are movable in different directions (e.g., parallel directions) to adjust the size of the aperture through which the radiation beam from the second source of radiation 30 passes, and also to adjust the beam 32 position relative to the patient to illuminate only the portion of the patient to be imaged for optimized imaging and minimized patient dose. For example, a collimator can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

In accordance with one embodiment, the shape of the radiation beam 32 from the second source of radiation 30 can be changed during an image acquisition. Stated differently, in accordance with one exemplary implementation, the collimator 36 leaf positions and/or aperture width can be adjusted before or during a scan. For example, in accordance with one embodiment, the collimator 36 can be selectively controlled and dynamically adjusted during rotation of the second source of radiation 30 such that the radiation beam 32 has a shape with sufficient primary/shadow regions and is adjusted to include only an object of interest during imaging (e.g., the prostate). The shape of the radiation beam 32 being emitted by the second source of radiation 30 can be selectively controlled before, during, and/or after a scan, depending on the desired image acquisition, which may be based on imaging and/or therapeutic feedback, as discussed in more detail below.

It will be further appreciated that the first source of radiation 20 can include or otherwise be associated with a beamformer or collimator. The collimator/beamformer associated with the first source of radiation 20 can be configured in a number of ways, similar to the collimator 36 associated with the second source of radiation 30.

The collimator assembly 36 can be controlled to adjust the shape of the radiation beam 32 emitted by the second source of radiation 30 in a number of geometries, including, but not limited to, a fan beam, thick fan beam, or cone beam having a beam thickness (width) as low as one detector row width or including multiple detector rows, which may be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. However, various other exposed and active area sizes or ratios of exposed-to-active detector area may be suitable in other embodiments.

In accordance with one exemplary embodiment, the radiotherapy device 10 has been described above as including a first source of radiation 20, a second source of radiation 30, a first radiation detector 24 positioned to receive radiation from the first source of radiation 20 and a second radiation detector 34 positioned to receive radiation from the second radiation source 30. It will be appreciated, however, that the radiotherapy device 10 can include a first source of radiation 20 (e.g., a source of therapeutic radiation), a second source of radiation 30 (e.g., a kV radiation source) and only a radiation detector 34 positioned to receive radiation from the second source of radiation 30 without departing from the scope of the disclosed technology.

The radiation source 20 may be mounted, configured, and/or moved into the same plane or a different plane (offset) than the radiation source 30. In some embodiments, scatter caused by simultaneous activation of the radiation sources 20, 30 may be incrementally reduced by offsetting the radiation planes. In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MV scatter on a kV detector.

Integrated as a radiotherapy device, apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, CBCT data, MRI data, PET data or 3D rotational angiography (3DRA) data, and/or any information obtained from these or other imaging modalities. In some embodiments, the device 10 can track in-treatment patient, target, or ROI motion.

A reconstruction processor 40 can be operatively coupled to the first detector 24 and/or second detector 34. In one embodiment, the reconstruction processor 40 is configured to generate patient images based on radiation received by detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The radiotherapy device 10 can include an operator/user interface 48, where an operator of the radiotherapy device 10 can interact with or otherwise control the radiotherapy device 10 to provide input relating to scan or imaging parameters and the like. The operator interface 48 can include any suitable input devices, such as a keyboard, mouse, voice-activated controller, or the like. The radiotherapy device 10 can also include a display 52 or other human-readable element to provide output to the operator of the radiotherapy device 10. For example, the display 52 can allow the operator to observe reconstructed patient images and other information, such as imaging or scan parameters, related to operation of the radiotherapy device 10.

It will be appreciated that the collimator assembly 36 positioned relative to the second source of radiation 30 can be configured to provide dynamic collimation of a radiation beam being emitted by the second radiation source 30.

The collimator assembly 36 can be controlled such that the beam 32 from the second radiation source 30 covers as much or as little of the second detector 34 based on the particular imaging task being carried out. For example, the collimator 36 can be selectively controlled to provide a fan beam having a fan thickness from a single detector row, which could be sub-millimeter, up to several centimeters, including, for example, a beam thickness of 3-4 centimeters (measured in the longitudinal direction in the detector plane). Such a beam configuration can be used in a continuous, helical fan-beam imaging mode in accordance with aspects of the disclosed technology. In other embodiments, circular imaging modes may be used, including with a larger fan beam or cone beam thickness. For example, for any mode, the collimator 36 can be selectively controlled to provide a beam having a thickness of about one centimeter. In accordance with another exemplary embodiment, the collimator 36 can be selectively controlled to provide a beam having a thickness of more than one centimeter or several centimeters, including, for example, between about two centimeters and about four centimeters. In accordance with another exemplary embodiment, the collimator 36 can be selectively controlled to provide a beam 32 having a thickness between about fifteen centimeters and about thirty centimeters. In accordance with another exemplary embodiment, the collimator 36 can be selectively controlled to provide a beam 32 having a thickness between about thirty-five centimeters and about forty centimeters. Generally, the system and beam geometry can be controlled to yield beams that are thin (e.g., single row), thick (e.g., multi-row), or cone-shaped.

In accordance with one implementation, the geometry of the beam 32 from the second radiation source 30 can be changed during an image acquisition. Stated differently, in accordance with one exemplary implementation, the collimator 36 leaf positions and/or aperture width can be adjusted before or during a scan. For example, in accordance with one embodiment, the collimator 36 can be selectively controlled and dynamically adjusted during rotation of the second radiation source 30 such that the beam 32 has a rectangular geometry that includes only an object of interest during imaging (e.g., the prostate).

As shown in FIG. 2, the radiotherapy device 10 includes a controller (indicated generally as 60) operatively coupled to one or more components of the radiotherapy system 10. The controller 60 controls the overall functioning and operation of the radiotherapy device 10, including providing power and timing signals to the first radiation source 20 and/or the second radiation source 30 and a gantry motor controller that controls rotational speed and position of the rotatable gantry 12. It will be appreciated that the controller 60 can encompass one or more of the following: a patient support controller, a gantry controller, a controller coupled to the first radiation source 20 and/or the second radiation source 30, a collimator assembly controller, a controller coupled to the first detector 24 and/or the second detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The radiotherapy system 10 may include various components, logic, and software. In one embodiment, the controller 60 comprises a processor, a memory, and software. By way of example and not limitation, a radiotherapy system (such as, for example, radiotherapy system 10 shown in FIGS. 1 and 2) can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Other routines include processes and/or algorithms associated with data and image processing, including, for example, the processes described below. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with a radiotherapy device 10 can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with radiotherapy device 10.

Radiotherapy device 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The first source of radiation 20 and/or second source of radiation 30 can be operatively coupled to a controller 60 configured to control the relative operation of the first source of radiation 20 and the second source of radiation 30. For example, the second source of radiation 30 can be controlled and operated simultaneously with the first source of the radiation 20. In addition, or alternatively, the second source of radiation 30 can be controlled and operated sequentially with the first source of radiation 20, depending on the particular treatment and imaging plan being implemented.

It will be appreciated that the second detector 34 can take on a number of configurations without departing from the scope of the disclosed technology. As illustrated in FIG. 2, the second detector 34 can be configured as a flat-panel detector (e.g., a multi-row flat panel detector). In accordance with another exemplary embodiment, the second detector 34 can be configured as a curved detector.

Regardless of the configuration or geometry of the second detector 34, it will be appreciated that the collimator assembly 36 positioned relative to or otherwise associated with the second source of radiation 30 can be selectively controlled to control the shape of the radiation beam 32 emitted by the second radiation source 30 to selectively expose part or all of the second radiation detector 34. For example, in accordance with one exemplary embodiment, the beam from the second source of radiation can be collimated or otherwise controlled to provide a fan or cone beam of imaging radiation. It will be appreciated that the size and geometry of the beam can be controlled based on the particular desired imaging application. In accordance with one example of the disclosed technology, the collimator assembly 36 can be selectively controlled such that the radiation beam 32 emitted by the second source of radiation is a fan beam, having a fan beam thickness greater than and down to about one centimeter. As discussed above, the geometry of the radiation beam 32 being emitted by the second radiation source can be changed during or after a scan, depending on the desired image acquisition, which may be based on imaging and/or therapeutic feedback.

It will be appreciated that the second source of radiation 30 and the second detector 34 positioned to receive radiation from the second source of radiation 30 can be configured to provide continuous rotation around the patient during an imaging scan. Further, synchronizing the motion and exposure of the second radiation source 30 with the longitudinal motion of the patient support can provide a continuous helical fan beam acquisition of a patient image during a procedure.

The following flow charts and block diagrams illustrate exemplary configurations and methodologies associated with CT and/or IGRT in accordance with the systems described above. The exemplary methodologies may be carried out in logic, software, hardware, or combinations thereof. In addition, although the procedures and methods are presented in an order, the blocks may be performed in different orders, including series and/or parallel. In particular, for example, the first and second radiation sources 20, 30 may be activated sequentially and/or simultaneously. Thus, the steps below, including imaging, image processing, image-based pre-delivery steps, and treatment delivery, although shown sequentially, may be executed simultaneously, including in real-time. Further, additional steps or fewer steps may be used.

Figure 3:
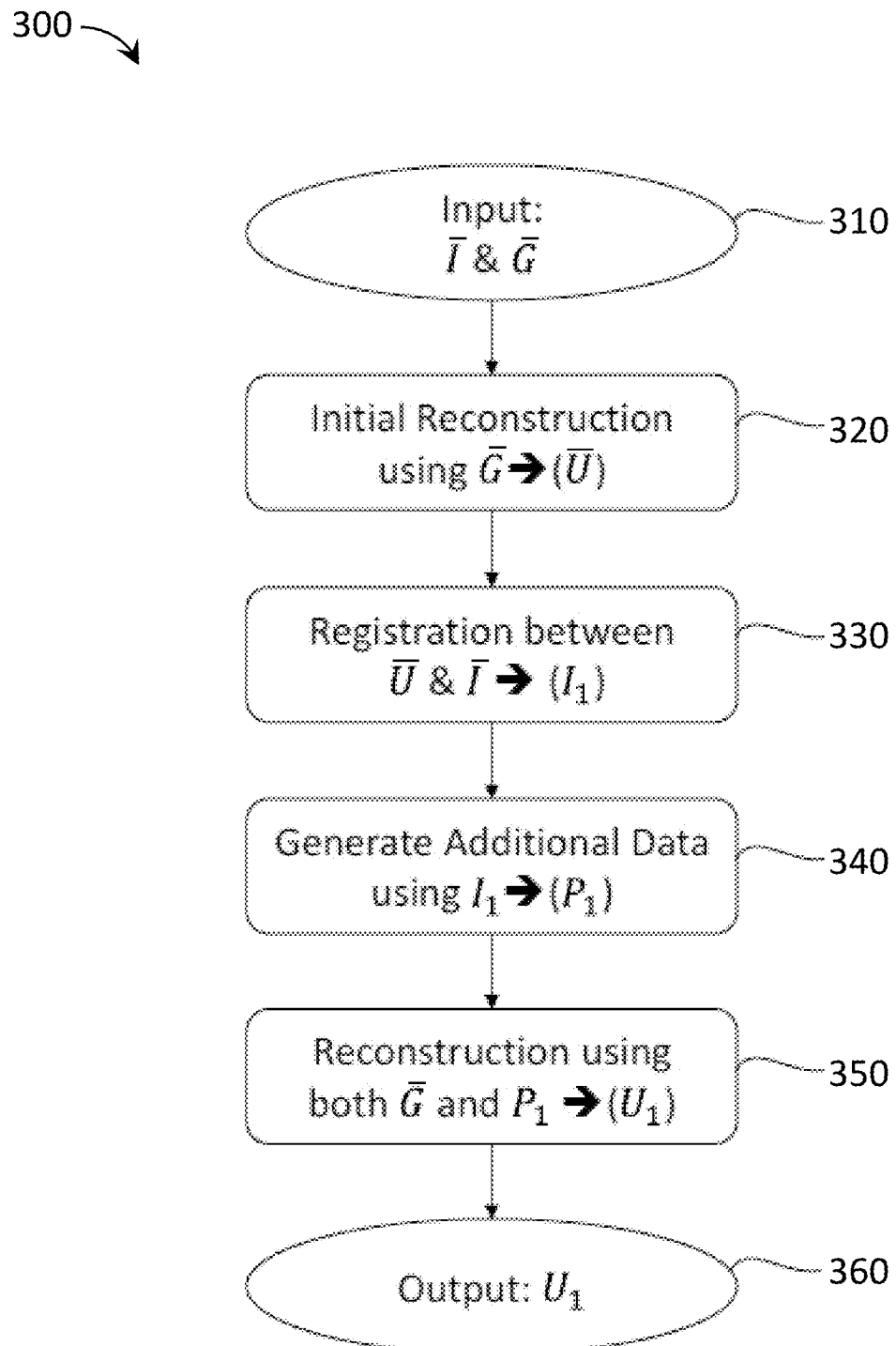
FIG. 3 is a flow chart depicting an exemplary method of generating an improved or corrected image.
Figure 4:
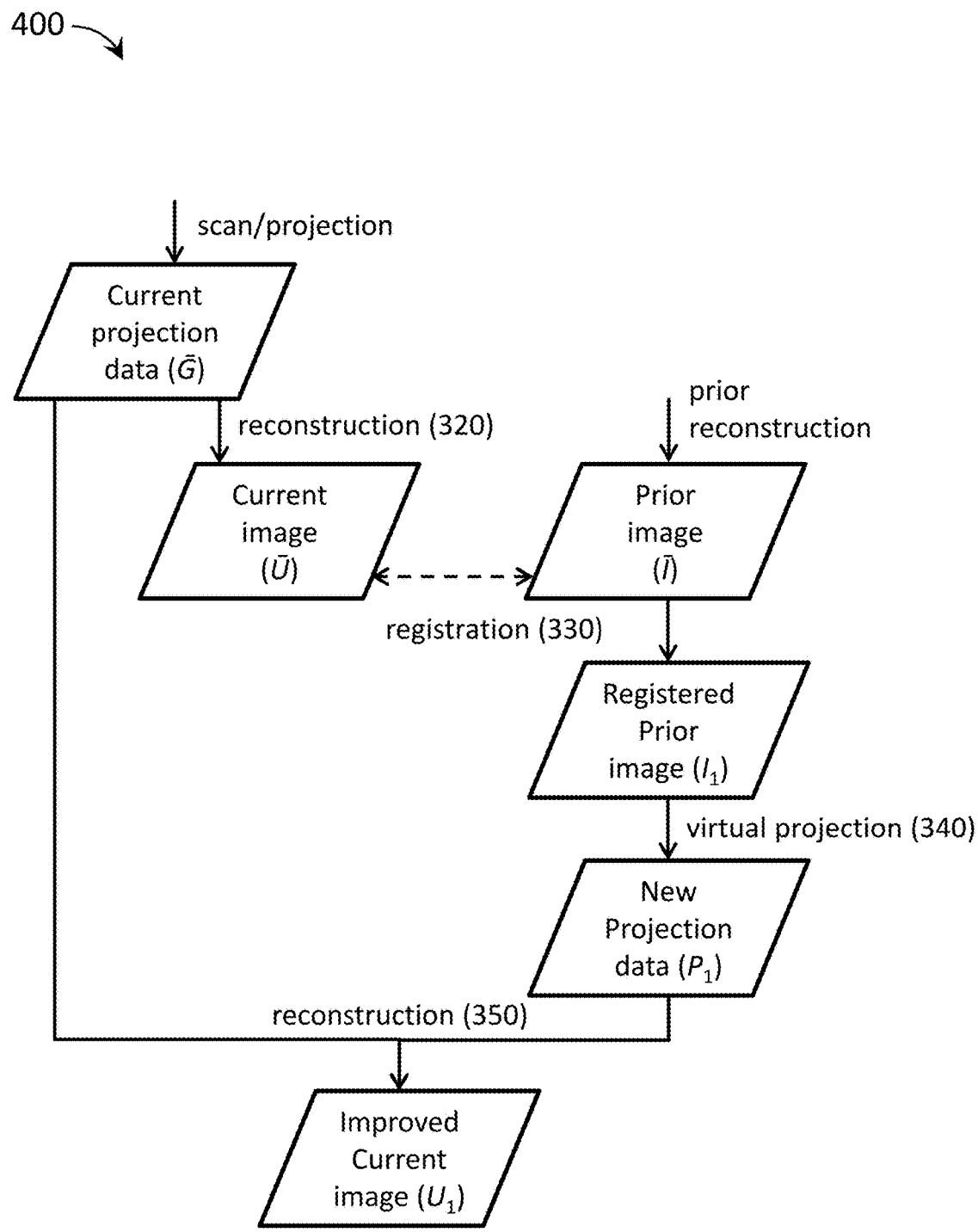
FIG. 4 is a block diagram showing exemplary data associated with aspects of the disclosed technology.

FIG. 3 is a flow chart of an exemplary method 300 for generating an improved or corrected image. This method 300 includes an image correction scheme that utilizes image registration and analytical reconstruction algorithms. FIG. 4 is a block diagram 400 showing exemplary data associated with method 300. With continued reference to FIG. 3 and FIG. 4, at step 310, input data includes, but is not limited to, the primary data acquired from the available source trajectory ($\overline{G}$) and a prior image ($\overline{I}$) (e.g., a previously-acquired planning CT image). For purposes of explanation of method 300, it is understood that such a source trajectory may not provide sufficient data for exact or sufficient image reconstruction in the volume of interest. It will be appreciated that additional input may include data acquisition parameters. In some embodiments, $\overline{G}$ and $\overline{I}$ are not transversally truncated or these transverse truncations can be well corrected. In other embodiments, it will be appreciated that the methods described herein can be applied to correction or image improvement based on transversely truncated projection data.

At step 320, an initial image reconstruction using the primary data ($\overline{G}$) can be performed, (e.g., using an approximate algorithm). For convenience, such an image is denoted as $\overline{U}$. It will be appreciated that this image $\overline{U}$ can contain image artifacts (e.g., cone-beam artifacts) due to data incompleteness. For example, for a circular trajectory, this first image $\overline{U}$ could be obtained by any suitable three-dimensional volume reconstruction technique, such as the Feldkamp-Davis-Kress (FDK) algorithm. For a helical trajectory, one possible reconstruction algorithm is weighted filtered-back-projection.

At step 330, image registration is performed between the initial reconstruction $\overline{U}$ and the prior/planning image $\overline{I}$. For purposes of this explanation, the registered prior/planning image is denoted as $I_1$.

Step 340 includes designing or otherwise generating an additional piece of source trajectory that will provide the missing data for improved image reconstruction of the targeted volume of interest. Then, along this additional source trajectory, a virtual forward projector is applied to $I_1$ to generate a set of new projection data, which is denoted as $P_1$. Such a forward projector could make use of one or more suitable methods (e.g., Siddon's or Joseph's method) without departing from the scope of the disclosed technology. In one embodiment, such a forward projection method can use the same data acquisition configurations as those of the primary data $\overline{G}$ to make sure $\overline{G}$ and $P_1$ are consistent.

It will be appreciated that the detector configuration for the additional piece, however, may allow different dimension and detector pixel size. Take the circular source trajectory as an example, such an additional piece of source trajectory can be a line or an arc connected to the circular trajectory, and the projector may include tube potential, tube current, spectrum, etc. For the helical trajectory, the additional source trajectory could be extended from the initial source trajectory in the longitudinal direction, and could be in the form of, for example, a helix, line and arc.

At step 350, an improved image reconstruction using both $\overline{G}$ and $P_1$ is performed. For purposes of discussion, the reconstructed image is denoted as $U_1$. This reconstructed image $U_1$ is then considered as the output of the basic correction scheme (indicated generally as 360). Taking the circular source trajectory as an example, with the help of the additional set of the projection data $P_1$ from the virtual line or arc, the Katsevich type reconstruction algorithm can be used to perform the reconstruction 350 to generate $U_1$. For the helical trajectory, the same reconstruction algorithm as used for the initial reconstruction may be used for the additional piece of trajectory. If the additional piece of trajectory is of different type, then the Katsevich type reconstruction algorithm may be used for the extended portion of volume of interest.

Figure 5:
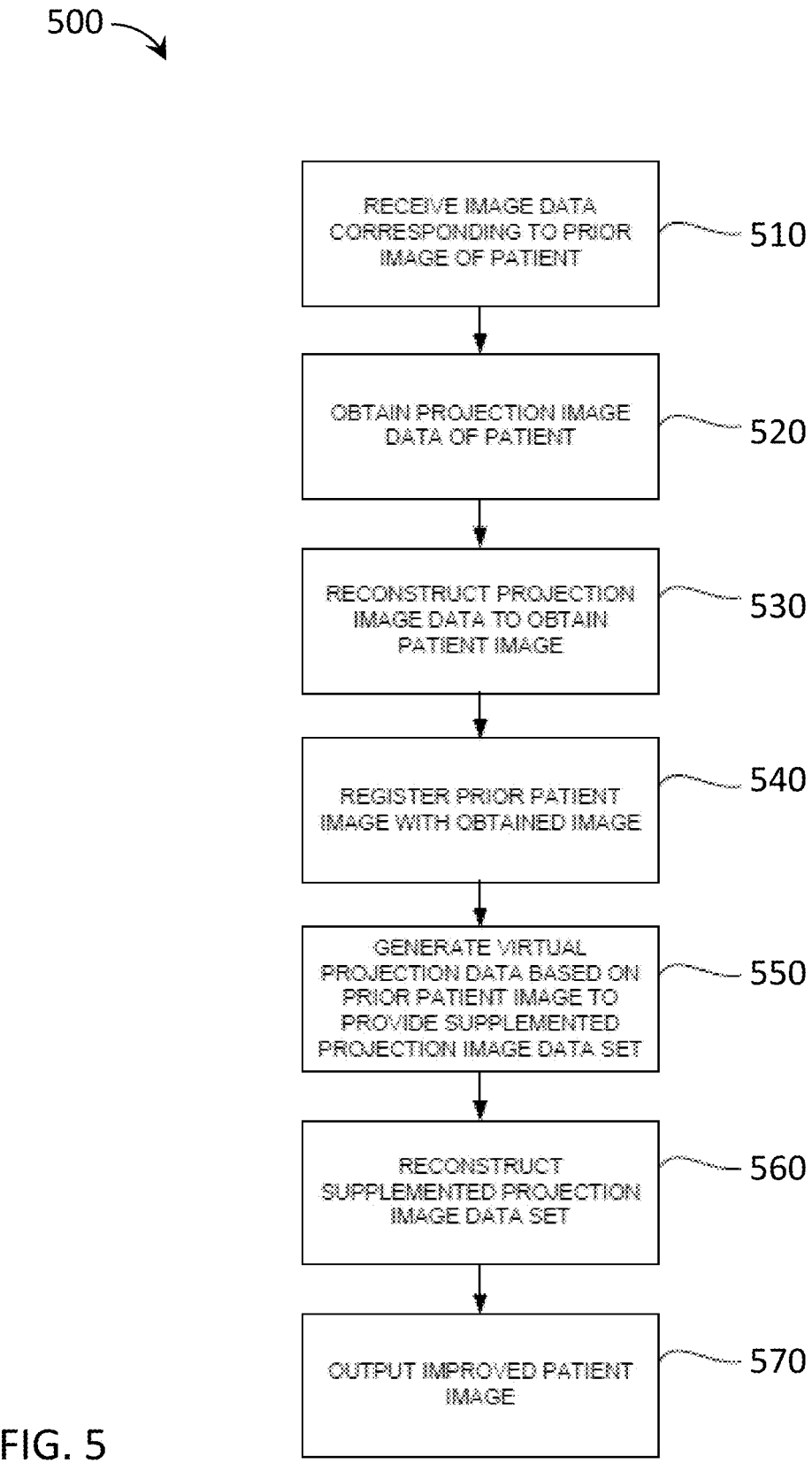
FIG. 5 is a flow chart depicting another exemplary method of generating an improved or corrected image.

Referring now to FIG. 5, a flowchart of an exemplary image processing/generation method 500 is provided. It will be appreciated that the image generation method 500 can include an imaging method (e.g., CT) in conjunction with an IGRT procedure in which a patient image can be captured before and/or during a treatment procedure. In one embodiment, the method 500 can be associated with the radiotherapy device 10, as described above. In such an exemplary case, the prior or otherwise previously-acquired image could be a pre-treatment or planning image. Alternatively, the imaging method 500 described in connection with FIG. 5 can be conducted independent of an IGRT application.

The method 500 begins at step 510 where image data corresponding to a prior or otherwise previously-acquired image of a patient is received. In accordance with one embodiment, the received image data can be a prior CT image (e.g., a planning image). Alternatively, the received image can be from another imaging modality (e.g., a magnetic imaging resonance (MR) image). In accordance with one embodiment, the received image data can be CT image data from a prior planning image collected for use with and in connection with an IGRT procedure.

At step 520, projection image data of a patient can be obtained (e.g., through a CT imaging operation, such as a kV imaging operation, a MV imaging operation, or the like, using, e.g., device 10). In accordance with one embodiment, the obtained projection image data might be truncated at least axially. In accordance with another embodiment, the obtained projection image data can be truncated transversely as well as axially. In yet other embodiments, the projection image data may include artifacts, instead of or in addition to truncated data. In some embodiments, the ability to use truncated data and/or data with artifacts can allow for faster scanning, which can also reduce image radiation doses. For example, in some embodiments, the ability to correct or improve on truncated data and/or data with artifacts allows the helical pitch to be increased, resulting in faster scanning in spite of the resulting defects.

At step 530, an image reconstruction can be performed based on the obtained projection image data of a patient to generate or obtain a patient image. It will be appreciated that any one of a number of reconstruction techniques/algorithms can be employed without departing from the scope of the disclosed technology. For example, the FDK algorithm can be employed together with a circular image acquisition trajectory, and weighted filtered-back-projection can be employed with a helical image acquisition trajectory.

At step 540, the prior image of the patient can be registered with the obtained (reconstructed) patient image (e.g., using any suitable process of applying geometric transformations and/or local displacements to align the respective images). It will be appreciated that any suitable method of image registration can be employed without departing from the scope of the disclosed technology. For example, the prior image of the patient can be registered with the obtained patient image using a suitable rigid image registration process (e.g., where pixels move and/or rotate uniformly so that every pixel-to-pixel relationship remains the same after the transformation). In accordance with another example, the prior image of the patient can be registered with the obtained patient image using a suitable deformable image registration process (e.g., where pixel-to-pixel relationships change).

At step 550, virtual projection data can be generated based on the prior or otherwise previously-acquired image (e.g., planning image) to provide a supplemented projection image data set, including the obtained projection image data of the patient and the virtual projection data. It will be appreciated that this step can include designing or otherwise employing an additional piece of source trajectory that will theoretically provide missing data for improved image reconstruction of a targeted volume of interest. Then along this additional source trajectory, a virtual forward projector can be applied to the registered prior or otherwise previously-acquired image to generate a set of new projection data. Such a forward projector could make use of one or more suitable methods (e.g., Siddon's method or Joseph's method) without departing from the scope of the disclosed technology. Such a forward projection method should use the same data acquisition configurations as those of the obtained projection image data to make sure that the image data sets are consistent.

It will be appreciated that the detector configuration for the additional piece, however, may allow different dimension and detector pixel size. Take the circular source trajectory as an example, such an additional piece of source trajectory can be a line or an arc connected to the circular trajectory, and the projector may include tube potential, tube current, spectrum, etc. For the helical trajectory, the additional source trajectory could be extended from the initial source trajectory in the longitudinal direction, and could be in the form of, for example, a helix, line and arc.

At step 560, the supplemented projection image data set can be reconstructed. Again, it will be appreciated that any number of reconstruction algorithms or methods can be deployed without departing from the scope of the disclosed technology. At step 570, an improved or otherwise supplemented patient image can be output for use in a number of diagnostic and/or treatment applications. The improved or otherwise supplemented patient image will be based on the supplemented projection image data. In this manner, the improved or otherwise supplemented patient image is based on image data not captured during the projection image data acquisition.

Figure 6:
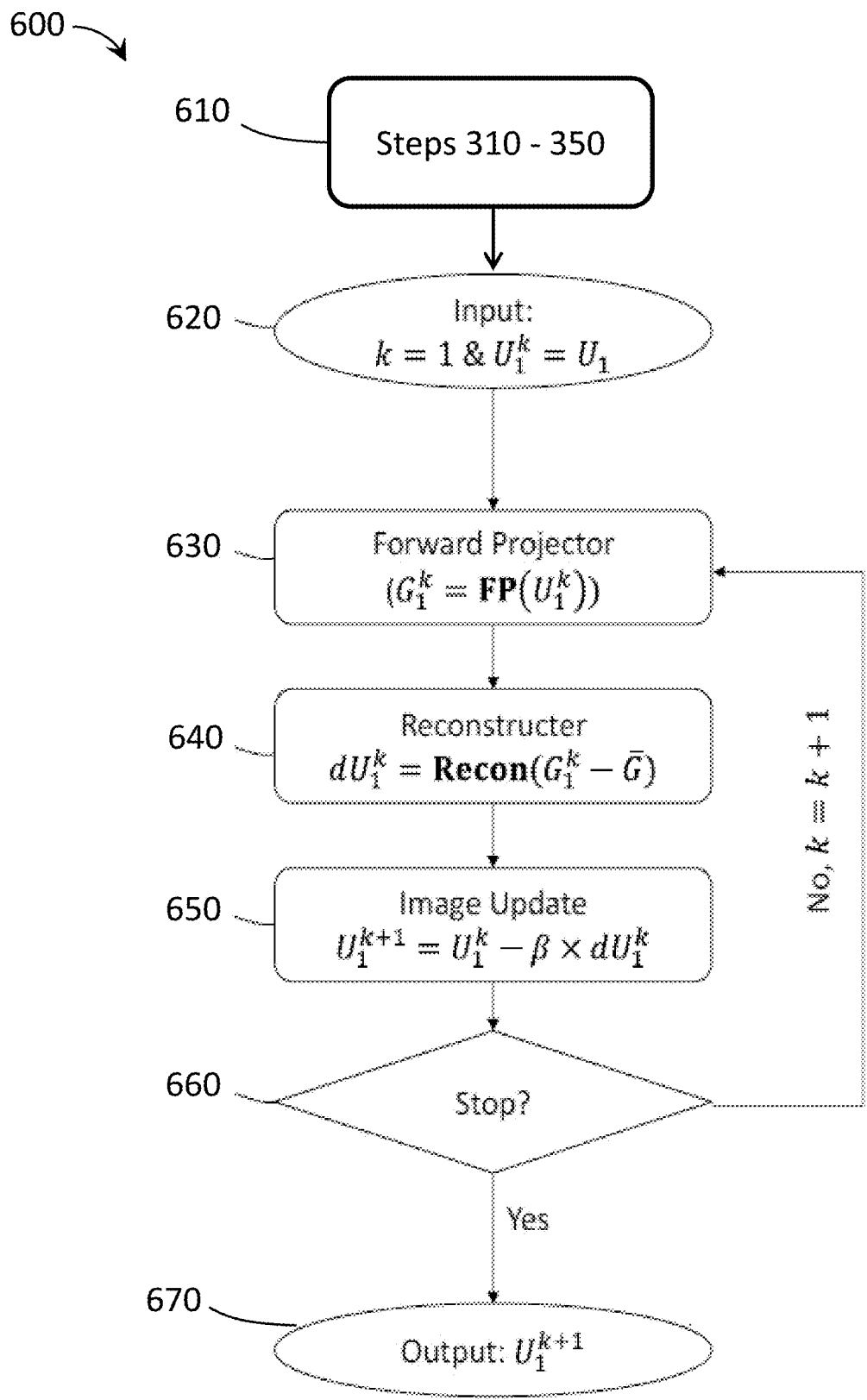
FIG. 6 is a flow chart depicting an exemplary method of generating an improved or corrected image with data consistency enforcement.

FIG. 6 is a flow chart of another exemplary method 600 for generating an improved or corrected image. This method 600 includes an image correction scheme that utilizes image registration, analytical reconstruction, and iterative reconstruction algorithms. Method 600 can expand on method 300 for enforced data consistency. For purposes of explanation, it will be appreciated that it is usually the case that the projection data and the prior/planning image are not consistent, as patient anatomy likely will not be the same between two different times. Therefore, it is possible that with an image improvement/correction method, for example, as described above with respect to FIG. 3, the image reconstructed using $P_1$ may result in new artifacts. Such a problem may be overcome by enforcing data consistency between the reconstruction and the primary projection data $\overline{G}$ using an iterative process.

Method 600 of FIG. 6 can utilize a corrected or improved image, for example, from steps 310 through 350 from FIG. 3, described above, shown as step 610. In particular, the input at 620 can include the output $U_1$ of method 300 shown in step 360 of FIG. 3. At step 620, k is set equal to 1 and $U_1^k$ is set equal to $U_1$.

For purposes of explanation, FP refers to forward projection and Recon refers to an analytical reconstruction algorithm, which can be the same as or different from the algorithm used for the initial reconstruction described above with respect to FIG. 3.

At step 630, the input image $U_1^k$ is forward projected, for example, using the same data acquisition configurations as those used for the primary projection data $\overline{G}$. For purposes of this explanation, the new projection data are denoted as $G_1^k$.

At step 640, the difference between the new projection data $G_1^k$ and the primary projection data $\overline{G}$ is calculated, which is reconstructed into a difference image. For purposes of explanation, the difference image is denoted as $dU_1^k$. It will be appreciated that various reconstruction algorithms may be used in this step without departing from the scope of the disclosed technology. It will be further appreciated that the reconstruction algorithms used may or may not be the same as the reconstruction algorithms used in step 320 of the method of FIG. 3 for the initial image reconstruction.

At step 650, the difference image $dU_1^k$ is then subtracted from the current image $U_1^k$. The amount of the subtracted value may be controlled or weighted by a parameter denoted as β. Any suitable value of β may be used to affect the iterative nature of the update. The updated image is then denoted as $U_1^{k+1}$.

At step 660, a decision is made on whether to stop the process based on certain criteria (giving rise to output $U_1^{k+1}$ at 670). Such a criterion may be called stopping criteria and could be, for example, a prescribed number of iterations or the magnitude of $dU_1^k$ is below a prescribed threshold. If the criteria for stopping at step 660 is not met, k is incremented to k+1 and the method 600 proceeds to step 630 for additional processing. The additional processing may be executed any number of times according to the criteria.

Figure 7:
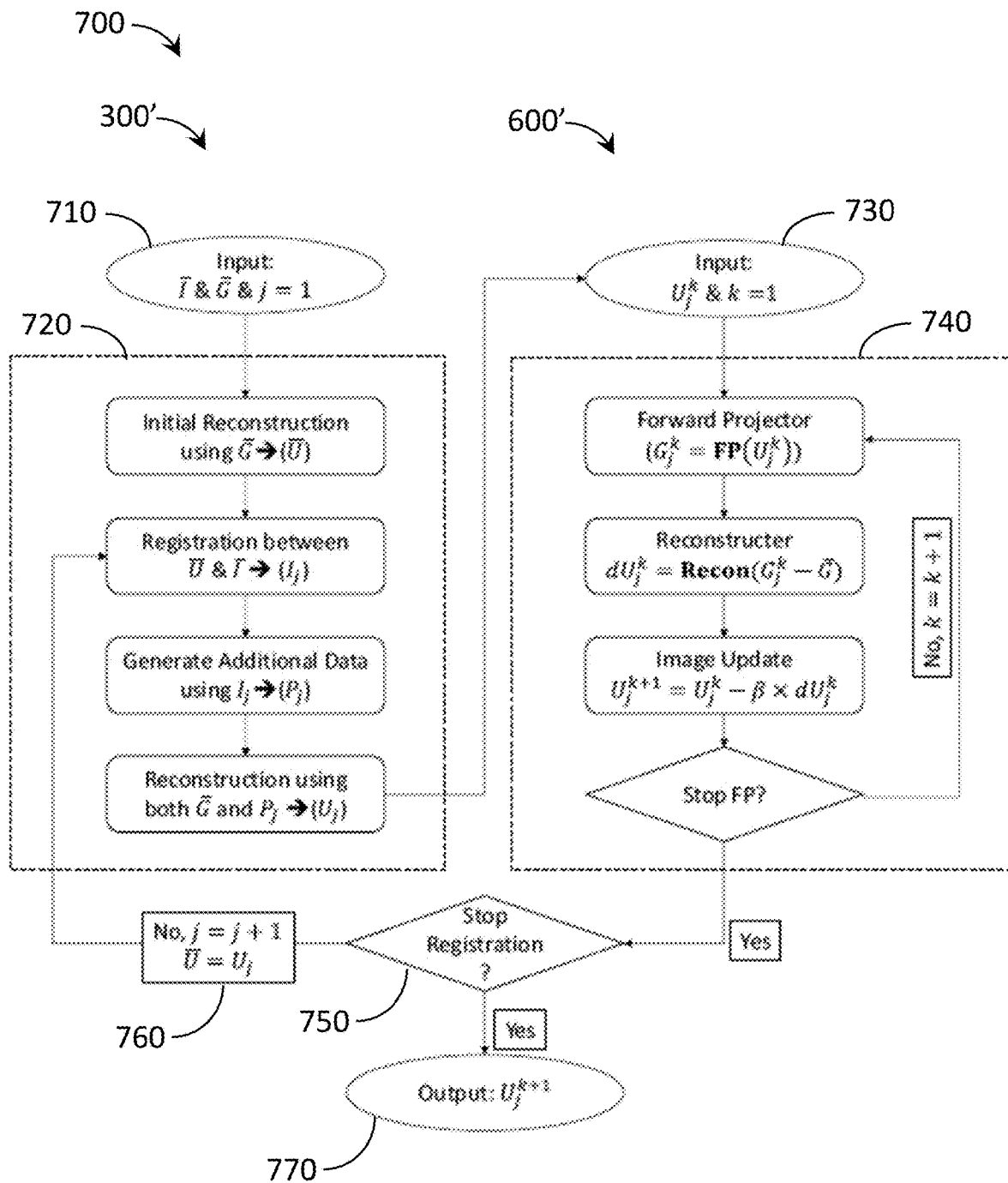
FIG. 7 is a flow chart depicting an exemplary method of generating an improved or corrected image with data consistency enforcement and prior image refinement.

FIG. 7 is a flow chart of another exemplary method 700 for generating an improved or corrected image. This method 700 includes an image correction scheme that utilizes image registration, analytical reconstruction, and iterative reconstruction algorithms. Method 700 can expand on method 600, additionally applying an iterative process to the correction scheme as well as the consistency enforcement. It will be appreciated that the method 700 illustrated in FIG. 7 includes a prior image refinement method. For example, the image generated by method 600 of FIG. 6, $U_1^{k+1}$, is likely better than the initial reconstruction V (referred to in FIG. 3), and, therefore, may be reused for registration to improve the result of both the method of FIG. 3 and the method of FIG. 6. Such a process can be achieved by adding an iterative process between the image improvement/correction method, for example, method 300 of FIG. 3 (indicated generally as 300' in FIG. 7) and the data consistency enforcement method, for example, method 600 of FIG. 6 (indicated generally as 600' in FIG. 7). As noted above, the method 700 of FIG. 7 includes a prior image refinement method. The iteration number (j) of this outer loop can be prescribed based on certain criteria. Such a criterion may be called stopping criteria and could be, for example, a prescribed number of iterations or the magnitude of change during step 740 (described below) is below a prescribed threshold. If this number is set to 1, it will be appreciated that the method of FIG. 7 becomes the method of FIG. 6.

In this embodiment, at step 710, method 700 executes step 310 and j is set equal to 1. Next step 720 executes steps 320 through 350, including based on iteration j to correct the image and refine the prior image. At step 730, method 700 executes step 620, including based on iteration j. Next step 740 executes steps 630 through 660, including its k loop and based on iteration j to enforce consistency. At step 750, method 700 determines whether to stop the registration loop. At step 760, if the criteria for stopping is not met, j is incremented to j+1, $\overline{U}$ is set to $U_j$, and the method 700 proceeds to intermediate step 330 (of step 720) for additional processing. At step 770, if the criteria for stopping at step 750 is met, the current image is output.

Figure 8:
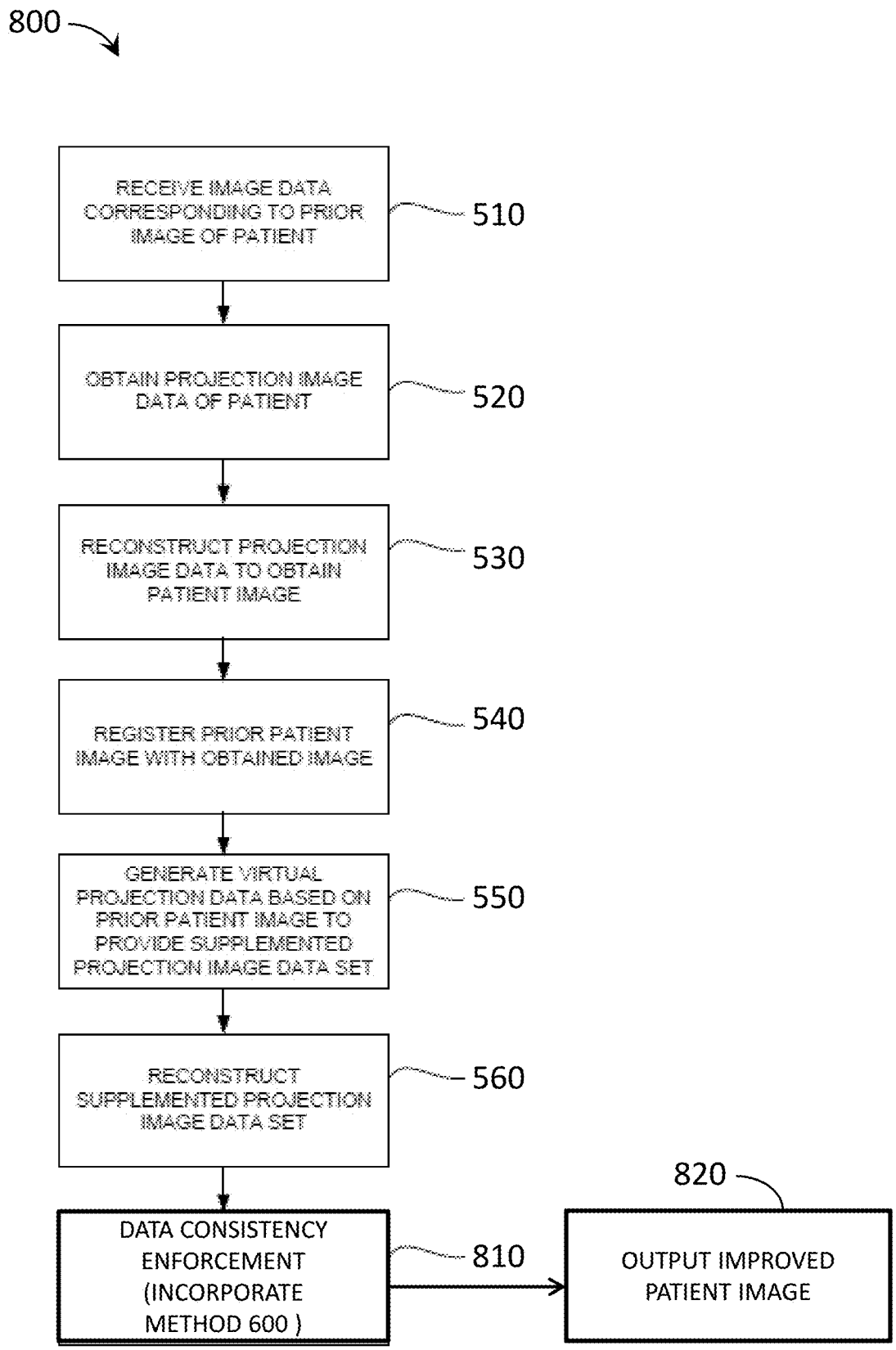
FIG. 8 is a flow chart depicting an exemplary method of generating an improved or corrected image with data consistency enforcement.
Figure 9:
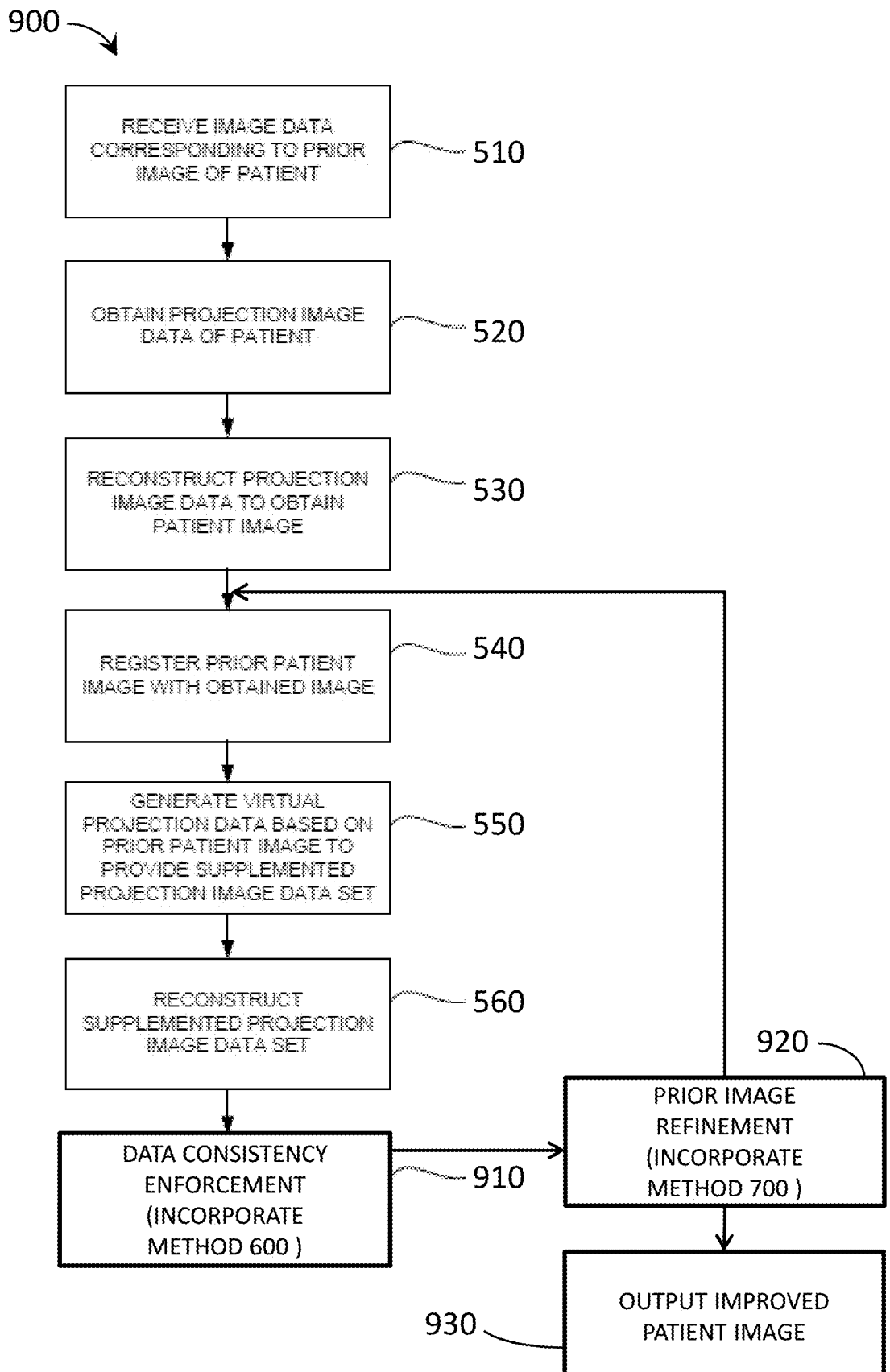
FIG. 9 is a flow chart depicting an exemplary method of generating an improved or corrected image with data consistency enforcement and prior image refinement.

Method 600 and/or method 700 may also be combined with method 500 to further improve the output patient image. For example, FIG. 8 is a flowchart of an exemplary image processing/generation method 800. This method 800 includes steps 510 through 560 from method 500, step 810 (which incorporates/combines method 600 as described above), and outputs an improved patient image at 820. FIG. 9 is a flowchart of another exemplary image processing/generation method 900. This method 900 includes steps 510 through 560 from method 500, step 910 (which incorporates/combines method 600 as described above), step 920 (which incorporates/combines method 700 as described above), and outputs an improved patient image at 930.

Figure 10:
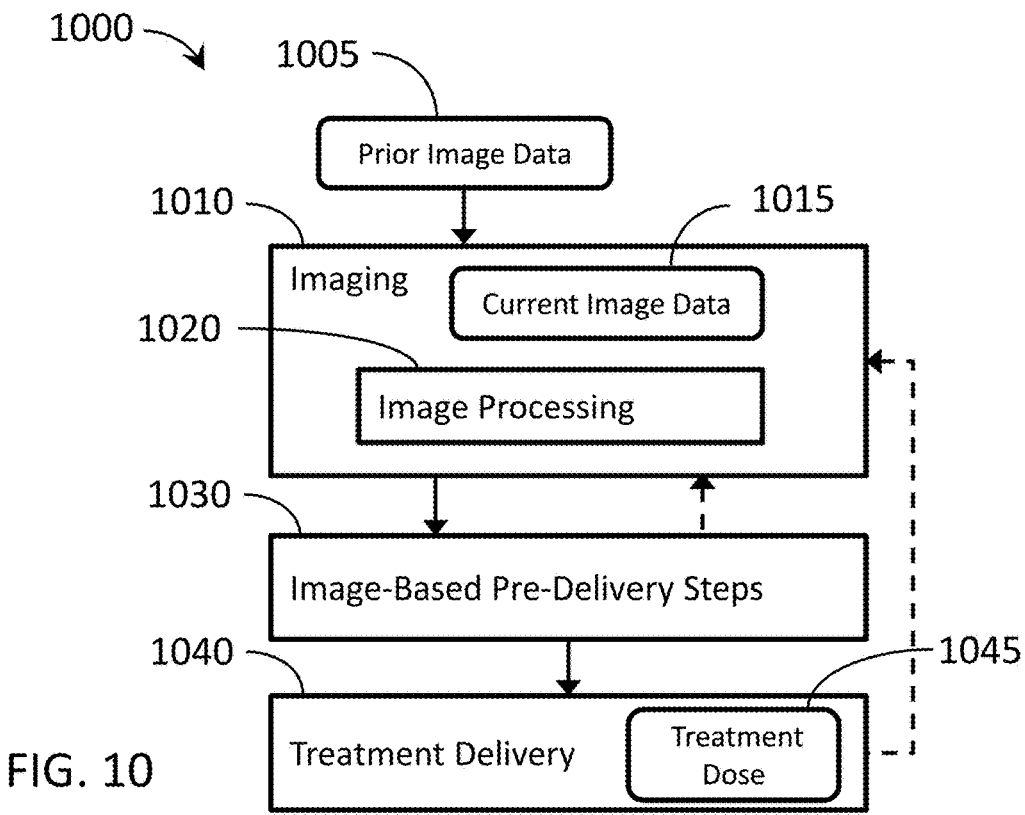
FIG. 10 is a flow chart depicting an exemplary method of IGRT using a radiotherapy device.

FIG. 10 is a flow chart depicting an exemplary method 1000 of IGRT using a radiotherapy device (e.g., radiotherapy device 10). Prior image data 1005 of the patient is available for use (e.g., a prior image ($\overline{I}$), which may be a previously-acquired planning image, including a prior CT image, as discussed above). Prior data 1005 can also include treatment plans, phantom information, models, a priori information, etc. In some embodiments, prior image data 1005 is generated by the same radiotherapy device, but at an earlier time. At step 1010, imaging of the patient is performed using a source of low-energy radiation (e.g., kV radiation from second radiation source 30). Step 1010 can produce image(s) or imaging data 1015 (e.g., input data that includes the primary data acquired from the available source trajectory ($\overline{G}$), as discussed above). In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1010 can also include image processing to generate patient images based on the imaging data (e.g., in accordance with the methods described above). Although image processing step 1020 is shown as part of imaging step 1010, in some embodiments image processing step 1020 is a separate step, including where image processing is executed by separate devices.

Next, at step 1030, one or more image-based pre-delivery steps, discussed below, are performed based at least in part on the imaging data 1015 from step 1010. As discussed in more detail below, step 1030 can include determining various parameters associated with the therapeutic treatment and (subsequent) imaging planning. In some embodiments, image-based pre-delivery steps (1030) may require more imaging (1010) before treatment delivery (1040). Step 1030 can include adapting a treatment plan based on the imaging data 1015 as part of an adaptive radiotherapy routine. In some embodiments, image-based pre-delivery steps 1030 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1040, therapeutic treatment delivery is performed using a source of high-energy radiation (e.g., MV radiation from first radiation source 20). Step 1040 delivers a treatment dose 1045 to the patient according to the treatment plan. In some embodiments, the IGRT method 1000 may include returning to step 1010 for additional imaging at various intervals, followed by image-based pre-delivery steps (1030) and/or treatment delivery (1040) as required. In this manner the imaging data 1015 may be produced and utilized during IGRT using one radiotherapy device 10 that is capable of adaptive therapy. As mentioned above, steps 1010, 1020, 1030, and/or 1040 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 11:
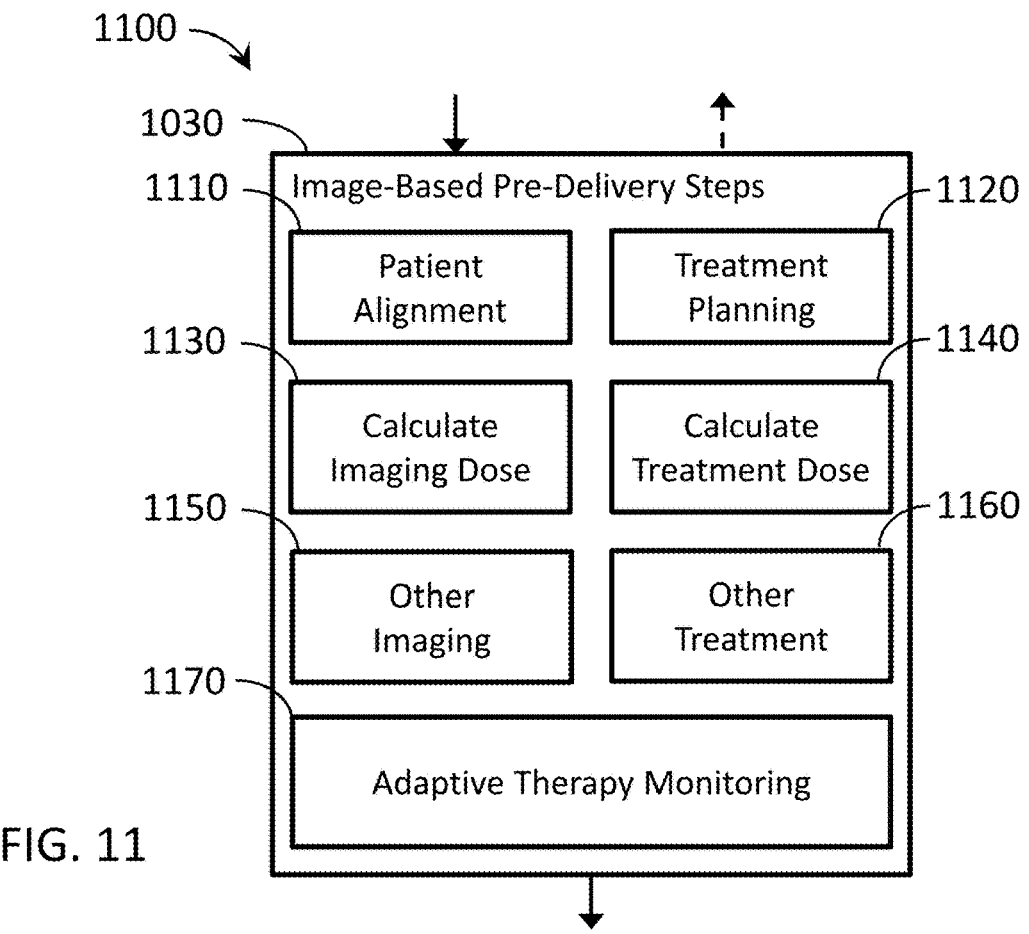
FIG. 11 is a block diagram depicting exemplary image-based pre-delivery steps.

FIG. 11 is a block diagram 1100 depicting exemplary image-based pre-delivery steps/options that may be associated with step 1030 above. It will be appreciated that the above-described radiotherapy device (e.g., radiotherapy device 10) can generate kV images that can be used in a variety of ways, including for image-based pre-delivery steps (1030), without departing from the scope of the present invention. For example, images 1015 generated by the radiotherapy device can be used to align a patient prior to treatment (1110). Patient alignment can include correlating or registering the current imaging data 1015 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the radiotherapy device can also be used for treatment planning or re-planning (1120). In various embodiments, step 1120 can include confirming the treatment plan, modifying the treatment plan, generating a new treatment plan, and/or choosing a treatment plan from a set of treatment plans (sometimes referred to as "plan of the day"). For example, if the imaging data 1015 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1015 (generated by the radiotherapy device 10 at step 1010), the imaging data 1015 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the radiotherapy device 10 can be used to calculate imaging dose (1130), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the radiotherapy device 10 can be used to calculate treatment dose (1140), which may be used for ongoing determinations of total dose to the patient and/or may be included as part of treatment planning or re-planning.

In accordance with other exemplary use cases, images generated by the radiotherapy device 10 can be used in connection with planning or adjusting other imaging (1150) and/or other treatment (1160) parameters or plans, including, for example, as part of adaptive therapy and/or treatment plan generation. In accordance with another exemplary use case, images generated by the radiotherapy device 10 can be used in connection with adaptive therapy monitoring (1170), which can include monitoring treatment delivery and adapting as required.

It should be appreciated that the image-based pre-delivery steps (1030) are not mutually exclusive. For example, in various embodiments, calculate treatment dose (1140) can be a step by itself and/or can be part of adaptive therapy monitoring (1170) and/or treatment planning (1120). In various embodiments, the image-based pre-delivery steps (1030) can be performed automatically and/or manually with human involvement.

Figure 12:
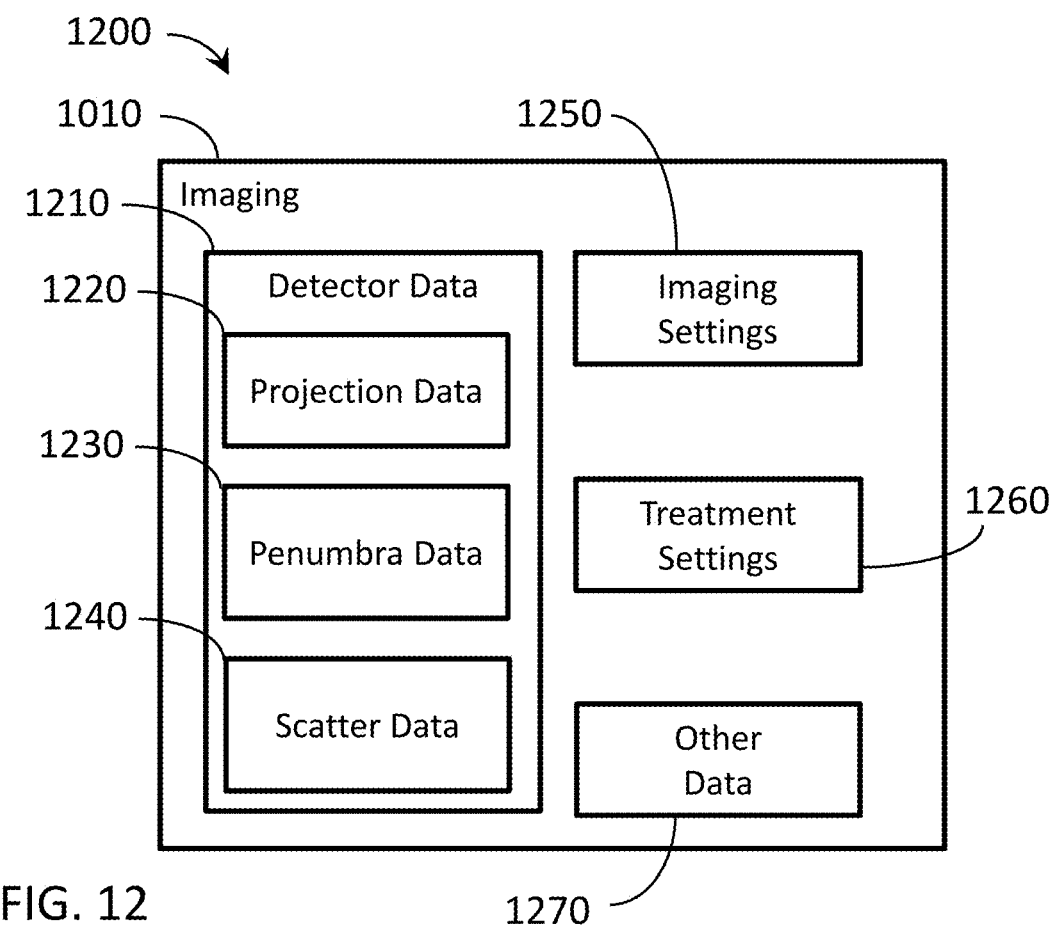
FIG. 12 is a block diagram depicting exemplary data that may be utilized during imaging or image-based pre-delivery steps.

FIG. 12 is a block diagram 1200 depicting exemplary data sources that may be utilized during imaging (1010) and/or subsequent image-based pre-delivery steps (1030), including treatment planning 1120, in addition to the prior data 1005. Detector data 1210 represents the data received by the image radiation detector 34. The projection data 1220 is the data generated by the radiation incident in the collimated beam area, which may be referred to as the primary region. The penumbra data 1230 is the data generated by the radiation incident in the penumbra region or area. The scatter data 1240 is the data generated by the radiation incident in a peripheral or scatter (only) region or area.

The penumbra data 1230 and/or the scatter data 1240 may be utilized to improve the quality of the images generated by the imaging step 1010. In some embodiments, the penumbra data 1230 and/or the scatter data 1240 may be combined with the projection data 1220 and/or analyzed in view of the applicable imaging settings 1250, treatment settings 1260 (e.g., if simultaneous imaging and treatment radiation), and any other data 1270 associated with the radiotherapy device 10 at the time of the data collection at the imaging detector 34. In other embodiments, the data may be used for the treatment planning step 1120.

As is discussed above, aspects of the disclosed technology relate to a computed tomography (CT) imaging system and method, where a prior or previously-acquired patient image (e.g., a planning image) can be used to supplement or otherwise improve an acquired CT image, wherein the acquired projection data representative of the acquired CT image might be truncated or otherwise incomplete/insufficient to accurately recover the scanned object/patient for exact and stable image reconstruction. The disclosed method avoids additional scanning to acquire data using one or more additional trajectories, thereby avoiding increased patient dose and avoiding complication of imaging workflow.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. A method for improving scan image quality using prior image data, the method comprising:
receiving image data corresponding to a prior image of a patient;
obtaining projection image data of the patient, wherein the obtained projection image data are truncated;
reconstructing a patient image based on the obtained projection image data of the patient;
registering the prior image with the reconstructed patient image;
generating virtual projection data based on the registered prior image; and
reconstructing a supplemented projection image data set to create an improved patient image, wherein the supplemented projection image data set comprises the obtained projection image data and the virtual projection data.

2. The method of claim 1, wherein the prior image of the patient is a computed tomography (CT) image.

3. The method of claim 2, wherein the prior image of the patient is a cone-beam CT image.

4. The method of claim 1, wherein the prior image of the patient is a magnetic resonance (MR) image.

5. The method of claim 1, wherein the prior image of the patient is a prior planning image of the patient.

6. The method of claim 1, wherein generating virtual projection data comprises extending at least one view of the obtained projection image data.

7. The method of claim 1, wherein generating virtual projection data comprises generating additional views to supplement the obtained projection image data.

8. The method of claim 7, wherein generating virtual projection data comprises setting a virtual source trajectory and obtaining a virtual projection of the registered prior image.

9. The method of claim 1, wherein the obtained projection image data is truncated axially and transversely.

10. The method of claim 1, wherein obtaining projection image data of the patient comprises obtaining projection image data of the patient using a continuous helical fan-beam computed tomography scan of the patient.

11. The method of claim 1, wherein registering the prior image with the reconstructed patient image includes performing a deformable image registration.

12. The method of claim 1, wherein registering the prior image with the reconstructed patient image includes performing a rigid image registration.

13. The method of claim 1, further comprising enforcing data consistency between the improved patient image and the obtained projection image data using an iterative process.

14. The method of claim 13, further comprising refining the registration of the prior image based on the improved patient image using an iterative process.

15. An imaging apparatus for improving scan image quality using prior image data, comprising:
a first radiation source configured for imaging radiation;
a radiation detector positioned to receive radiation from the first radiation source; and
a processor, wherein the processor comprises logic for:
receiving image data corresponding to a prior image of a patient;
obtaining projection image data of the patient from the radiation detector, wherein the obtained projection image data is truncated;
reconstructing a patient image based on the obtained projection image data of the patient;
registering the prior image with the reconstructed patient image;
generating virtual projection data based on the registered prior image; and
reconstructing a supplemented projection image data set to create an improved patient image, wherein the supplemented projection image data set comprises the obtained projection image data and the virtual projection data.

16. The apparatus of claim 15, further comprising a rotatable gantry system positioned at least partially around a patient support, wherein the first radiation source and the radiation detector are mounted to the rotatable gantry system, and wherein obtaining projection image data of the patient comprises obtaining projection image data of the patient using a continuous helical fan-beam computed tomography scan of the patient.

17. The apparatus of claim 15, further comprising a C-arm gantry system or at least one robotic arm positioned at least partially around a patient support, wherein the first radiation source and the radiation detector are mounted to the C-arm gantry system or the at least one robotic arm.

18. The apparatus of claim 15, further comprising a second radiation source configured for therapeutic radiation, wherein the first radiation source comprises an energy level less than the second radiation source, and wherein the processor further comprises logic for delivering a dose of therapeutic radiation to the patient via the second radiation source based on the improved patient image.

19. The apparatus of claim 18, wherein the first radiation source comprises a kilovoltage (kV) radiation source and the second radiation source comprises a megavoltage (MV) radiation source.

20. A radiotherapy delivery device comprising:
a rotatable gantry system positioned at least partially around a patient support;
a first radiation source coupled to the rotatable gantry system, the first radiation source configured for imaging radiation;
a second radiation source coupled to the rotatable gantry system, the second radiation source configured for therapeutic radiation, wherein the first radiation source comprises an energy level less than the second radiation source;
a radiation detector coupled to the rotatable gantry system and positioned to receive radiation from at least the first radiation source;
a data processing system configured for:
  receiving image data corresponding to a prior image of a patient;
  obtaining projection image data of the patient from the radiation detector, wherein the obtained projection image data is truncated;
  reconstructing a patient image based on the obtained projection image data of the patient;
  registering the prior image with the reconstructed patient image;
  generating virtual projection data based on the registered prior image;
  reconstructing a supplemented projection image data set to create an improved patient image, wherein the supplemented projection image data set comprises the obtained projection image data and the virtual projection data; and
  delivering a dose of therapeutic radiation to the patient via the second radiation source based on the improved patient image during adaptive IGRT.

* * * * *